United States Patent
Kosmecki et al.

(10) Patent No.: US 10,706,610 B2
(45) Date of Patent: *Jul. 7, 2020

(54) METHOD FOR DISPLAYING AN OBJECT

(71) Applicant: Scopis GmbH, Berlin (DE)

(72) Inventors: Bartosz Kosmecki, Berlin (DE); Andreas Reutter, Berlin (DE); Christopher Özbek, Berlin (DE)

(73) Assignee: Scopis GmbH, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/784,303

(22) Filed: Oct. 16, 2017

(65) Prior Publication Data

US 2018/0053335 A1 Feb. 22, 2018

Related U.S. Application Data

(63) Continuation of application No. 14/128,950, filed as application No. PCT/EP2012/062623 on Jun. 28, 2012, now Pat. No. 9,792,721.

(30) Foreign Application Priority Data

Jun. 28, 2011 (DE) ............ 10 2011 078 212

(51) Int. Cl.
*G06T 15/08* (2011.01)
*G06T 7/33* (2017.01)
(Continued)

(52) U.S. Cl.
CPC .......... *G06T 15/08* (2013.01); *A61B 1/00009* (2013.01); *A61B 1/04* (2013.01);
(Continued)

(58) Field of Classification Search
CPC .......... G06T 15/08; G06T 7/33; A61B 8/463; A61B 8/469
See application file for complete search history.

(56) References Cited

U.S. PATENT DOCUMENTS 6,019,724 A 2/2000 Gronningsaeter et al.
6,190,395 B1 2/2001 Williams
(Continued)

FOREIGN PATENT DOCUMENTS

DE 10015826 A1 10/2001
DE 102005012295 A1 9/2006
(Continued)

OTHER PUBLICATIONS

Leven et al., DaVinci Canvas: A Telerobotic Surgical System with Integrated, Robot-Assisted, Laparoscopic Ultrasound Capability, 2005, Springer-Verlag Berlin Heidelberg 2005, pp. 811-818 (Year: 2005).*

(Continued)

*Primary Examiner* — Samantha (Yuehan) Wang
(74) *Attorney, Agent, or Firm* — Howard & Howard Attorneys PLLC

(57) ABSTRACT

A method and a device for displaying an object, in particular biological tissue. The method has the following steps: a) generating a first image of at least one sub-region of the object using a first device; b) generating a second image of at least one sub-region of the object using a second device; c) ascertaining first coordinates of at least some image points of the second image in a first coordinate system; d) ascertaining second coordinates of the image points of the second image by projecting the first coordinates in a second coordinate system which is different from the first coordinate system and which is assigned to the first device; and e) generating a combined image of the object from the first and the second image using the ascertained second coordinates of the image points of the second image.

21 Claims, 4 Drawing Sheets

(51) Int. Cl.

| | |
|---|---|
| *A61B 1/04* | (2006.01) |
| *A61B 1/00* | (2006.01) |
| *A61B 8/00* | (2006.01) |
| *A61B 8/08* | (2006.01) |
| *A61B 5/06* | (2006.01) |
| *G06T 11/60* | (2006.01) |
| *G06T 15/50* | (2011.01) |
| *A61B 34/20* | (2016.01) |
| *A61B 90/00* | (2016.01) |
| *A61B 6/03* | (2006.01) |
| *A61B 6/00* | (2006.01) |

(52) U.S. Cl.
CPC ............ *A61B 5/065* (2013.01); *A61B 8/4254* (2013.01); *A61B 8/5261* (2013.01); *G06T 7/33* (2017.01); *G06T 11/60* (2013.01); *G06T 15/50* (2013.01); *A61B 6/03* (2013.01); *A61B 6/5247* (2013.01); *A61B 8/463* (2013.01); *A61B 8/466* (2013.01); *A61B 8/469* (2013.01); *A61B 8/483* (2013.01); *A61B 2034/2055* (2016.02); *A61B 2090/365* (2016.02); *A61B 2090/378* (2016.02); *G06T 2207/10068* (2013.01); *G06T 2207/10136* (2013.01); *G06T 2207/20221* (2013.01); *G06T 2207/30004* (2013.01)

(56) References Cited

U.S. PATENT DOCUMENTS

| | | |
|---|---|---|
| 6,301,495 B1 | 10/2001 | Gueziec et al. |
| 6,466,815 B1 | 10/2002 | Saito et al. |
| 6,850,794 B2 | 2/2005 | Shahidi |
| 7,379,077 B2 | 5/2008 | Bani-Hashemi et al. |
| 7,605,826 B2 | 10/2009 | Sauer |
| 7,634,304 B2 | 12/2009 | Falco et al. |
| 7,844,320 B2 | 11/2010 | Shahidi |
| 7,993,353 B2 | 8/2011 | Roßner et al. |
| 7,995,076 B2 | 8/2011 | Emam et al. |
| 8,126,223 B2 | 2/2012 | Coste-Maniere et al. |
| 8,641,621 B2 * | 2/2014 | Razzaque ............ A61B 34/20 600/407 |
| 9,138,165 B2 | 9/2015 | Holsing et al. |
| 9,314,188 B2 | 4/2016 | Hladio et al. |
| 9,398,936 B2 | 7/2016 | Razzaque et al. |
| 9,510,771 B1 | 12/2016 | Finley et al. |
| 9,641,808 B2 | 5/2017 | Rose et al. |
| 9,646,423 B1 | 5/2017 | Sun et al. |
| 9,792,721 B2 * | 10/2017 | Kosmecki ................ A61B 1/04 |
| 2001/0051761 A1 | 12/2001 | Khadem |
| 2003/0210812 A1 | 11/2003 | Khamene et al. |
| 2008/0071142 A1 | 3/2008 | Gattani et al. |
| 2008/0095421 A1 | 4/2008 | Sun et al. |
| 2009/0318756 A1 | 12/2009 | Fisher et al. |
| 2010/0210902 A1 | 8/2010 | Navab et al. |
| 2010/0295931 A1 | 11/2010 | Schmidt |
| 2012/0280988 A1 | 11/2012 | Lampotang et al. |
| 2013/0245460 A1 | 9/2013 | King et al. |
| 2014/0193056 A1 | 7/2014 | Neff |
| 2014/0275975 A1 | 9/2014 | Coste-Maniere et al. |
| 2014/0330115 A1 | 11/2014 | Schildkraut et al. |
| 2016/0008083 A1 | 1/2016 | Kesten et al. |
| 2016/0120609 A1 | 5/2016 | Jacobsen et al. |
| 2016/0270863 A1 | 9/2016 | Makower |
| 2016/0360117 A1 | 12/2016 | Elefteriu et al. |
| 2017/0007350 A1 | 1/2017 | Popovic et al. |

FOREIGN PATENT DOCUMENTS

| | | |
|---|---|---|
| DE | 102010040518 A1 | 4/2011 |
| DE | 102010042540 A1 | 4/2012 |
| WO | 2011063266 A2 | 5/2011 |

OTHER PUBLICATIONS

Cheung et al, Fused Video and Ultrasound mages for Minimally Invasive Partial Neprectomy: A Phantom Study, MICCAI 2010, Part III, pp. 408-415, 2010.

Carling L. Cheung et al: Fusion of stereoscopic video and laparoscopic ultrasound for minimally invasive partial nephrectomy, 2010.

Joshua Leven et al: Da Vinci Canvas: A Telerobotic Surgical System with Integrated; Robot-Assistend, Laparoscopic Ultrasound Capability, 2005.

Tobias Sielhorst et al: Advanced Medical Displays: A Literature Review of Augmented Reality, Dec. 2008.

Shahidi, Ramin et al., "Implementation, Calibration and Accuracy Testing of an Image-Enhanced Endoscopy System", IEEE Transations on Medical Imaging, vol. 21, No. 12, Dec. 2002, pp. 1524-1535.

Winne, Ch. et al., "Overlay Visualization in Endoscopic ENT Surgery", Int. J. CARS, vol. 5 (Suppl 1), 2010, pp. S269-S270.

Baumhauer, M. et al., "Navigation in Endoscopic Soft Tissue Surgery—Perspectives and Limitations", Journal of Endourology, vol. 27, Issue 4, Apr. 17, 2008, pp. 1-15.

Caversaccio, M.D., Marco et al., "Computer-Assistance for Intraoperative Navigation in ENT Surgery", Minimally Invasive Therapy & Allied Technologies, vol. 12, Issue 1-2, 2003, pp. 1-40.

Freysinger, W. et al., "Image-Guided Endoscopic ENT Surgery", Eur Arch Otorhinolaryngol, vol. 254, 1997, pp. 343-346.

Wormald, Peter-John, "Surgery for the Frontal Recess and Frontal Sinus", Rhinology, vol. 43, 2005, pp. 82-85.

Hayashibe, Mitsuhiro et al., "Laser-Pointing Endoscope System for Intra-Operative 3D Geometric Registration", Proceedings of the 2001 IEEE International Conference on Robotics & Automation, Seoul, Korea, May 21-26, 2001, pp. 1543-1548.

Staub, Christoph et al., "Automation of Tissue Piercing Using Circular Needles and Vision Guidance for Computer Aided Laparoscopic Surgery", 2010 IEEE International Conference on Robotics and Automation, Anchorage Convention District, May 3-8, 2010, pp. 4585-4590.

* cited by examiner

METHOD FOR DISPLAYING AN OBJECT

CROSS-REFERENCE TO A RELATED APPLICATION

This application is a continuation of U.S. patent application Ser. No. 14/128,950, filed on Apr. 16, 2104, which was a National Phase Patent Application of International Patent Application Number PCT/EP2012/062623, filed on Jun. 28, 2012, which claimed priority of German Patent Application Number 10 2011 078 212.5, filed on Jun. 28, 2011.

BACKGROUND

The invention relates to a method for displaying an object, in particular a biological tissue, and the device for displaying an object.

Ultrasound and endoscopy devices are known from the medical technology, which allow an operative intervention using ultrasound control or visual control. For example U.S. Pat. No. 6,019,724 A discloses a corresponding ultrasound device.

SUMMARY

The object of the invention is to provide a method, which allows for a control of an intervention taking place at an object as good as possible. Furthermore, a corresponding device shall be provided.

According to an exemplary embodiment of the invention, a method for displaying an object, in particular a biological tissue, is provided with the steps:
a) Generating a first image of at least a sub-region of the object by means of a first device;
b) Generating a second image of at least one (possibly other) sub-region of the object by means of a second device, wherein the second image shows for instance a sub-region, which is a section of the sub-region of the object displayed in the first image or is identical to said sub-region;
c) Ascertaining first coordinates of at least some image points of the second image in a first coordinate system;
d) Ascertaining second coordinates of the image points of the second image by projecting the (ascertained) first coordinates into a second coordinate system, which is different from the first coordinate system and which is assigned to the first device; and
e) Generating a combined image of the object from the first and the second image by using the ascertained second coordinates of the image points of the second image.

The first and the second device are designed in particular for intraoperative imaging. The first and the second image, which is generated by the first or the second device, is obtained for instance by displaying (projecting) at least a sub-region of the object in an image plane or by a 3D display of the object. For instance, the first image is an endoscopy image or a stereo endoscopy image and the first device is accordingly an endoscopy device. It is of course also conceivable that the first device is not an endoscopy device.

The second image is for instance an ultrasound image, a MRT image, a x-ray image, a nuclear radiological image, a MRT image and/or a single photon emission tomography image and accordingly the second device is an ultrasound device, a MRT device, a x-ray device, a nuclear radiological device, a MRT device and/or a single photon emission tomography device (single photon emission computed tomography (SPECT)).

Ascertaining the second coordinates of the image points of the second image in the second coordinate system allows in particular perspective correct (in correct position) integration of at least a part of the second image into the first image.

The first device comprises for instance an optical system (for instance a camera), wherein for instance the second coordinate system is assigned to an image plane of the optical system. The optical system of the first device is for instance a video camera (for instance a CCD camera) with which a real time image of the object to be examined can be generated. In analogy a real time image can also be generated by means of the second device such that a combined real time image of the object can be realized.

The object to be displayed is in particular a biological tissue (for instance a soft tissue), wherein the method according to the invention can be used for controlling an operation of the tissue (for instance a removal of a tumor like a myoma) that means intraoperative. It is however also conceivable that the method according to the invention is used in non-medical applications for instance for a control of a repair of a component.

By a perspective correct combination of the image data of the first and the second device (for instance of endoscopy and ultrasound image data) for instance a depth impression of the relevant operation area is provided to a surgeon in addition to the endoscopy image. The surgeon can for instance assess by means of the combined image a depth extension of a tumor, which is not recognizable in a mere endoscopy image. Due to the additional depth information the surgeon is for instance able to update his planning of the operation or the result in the course of the operation.

The second coordinate system, into which the coordinates of the image points of the second image are projected, is for instance a two dimensional coordinate system, which is for instance assigned to an image plane of a camera of the first device. In the image plane of the camera for instance a CCD-chip is located, as already mentioned above, wherein for instance the origin of the second coordinate system is in a plane, which corresponds to a plane along which the CCD-chip extends, that means the coordinate axis of the second coordinate system continue in a plane, the position thereof corresponds to the image plane of the camera of the first device. It is also conceivable, that the first device is a stereo endoscopy device, which generates two perspective different images by means of two optical systems (cameras). In this case a projection of the first coordinates of the second image into the (second) coordinate system, which is assigned to the image plane of the first camera, as well as into the (further second) coordinate system, which is assigned to the image plane of the second camera in order to be able to integrate the second image in a correct position into both images of the stereo endoscopy device.

The projection of the first coordinates into the second coordinate system is effected in particular by means of a projection (in particular by means of a transformation), which is determined by calibrating the first device (for instance in form of an endoscopy device). This projection is in particular based on a model of the first device (in particular an optical system of the first device), wherein parameters of the optical system are determined by the calibration. For example a calibration pattern with the first device is projected for calibration, wherein the spatial coordinates of the calibration pattern (for instance relative to the first device) are determined by means of a position determining device and are assigned to the coordinates of the image of the calibration pattern in the image plane of the first device. A suitable calibration method, in particular for a first device in form of an endoscopy device, which can also be used for calibrating a distance determining device of an endoscopy device, is described in the German patent application DE 10 2010 042 540.0 from 15 Oct. 2010, which is in so far explicitly referenced.

By calibrating the first device a distortion of the object is also detected by an optic of the first device, i.e. for instance distortion parameters of the mentioned model of the optical system of the first device are also ascertained. The projection of the first coordinates of the image points of the second image into the second coordinate system is effected in particular by using said distortion parameters, i.e. a distortion function.

The calibration of the first device as well as the calibration of the second device is effected for instance by using in each case a calibration body, wherein the calibration bodies (for instance in one piece) are connected to each other (i.e. form an assembly), wherein the spatial position of the calibration bodies can be determined in particular via a position determining device.

According to a further exemplary modification of the invention ascertaining the second coordinates of the image points of the second image comprises the determination of the spatial position of the second device (for instance ultrasound head of an ultrasound device) by means of a position determining device and a projection of the first coordinates of the image points in spatial coordinates in a spatial coordinate system ("world coordinate system") assigned to the position determining device. The position determining device is for instance a clinical navigation system or a part of a clinical navigation system, which allows a determination of the spatial position (i.e. the position and the alignment) of an object such as the ultrasound head by using marking elements (which are arranged in particular at the second device, for instance an ultrasound head) and a measurement instrument (like in particular a measuring camera or magnetic field sensor). The assignment of the image data of the second device to spatial coordinates (which correspond to the spatial coordinates of points of the object displayed in the second image) is effected in particular after a corresponding calibration of the second device.

Active (self-luminous) elements, as for instance LEDs, passive (non-self-luminous elements), as for instance reflecting balls, films, specific patterns (target marks, laser gravures or native patterns as corners and edges) or magnetic field sources (for instance in form of current flown coils) can be used as marking elements. The attachment of a measuring instrument and marking elements can also be exchanged for position determination, i.e. the measuring instrument can be attached to the respective device and the marking elements can be positioned in space, as this is the case for instance in case of a mobile terminal instrument, which detects optically marking elements stationary placed in space or in case of a magnetic field sensor, which detects a magnetic field radiating into space with marking functions.

A measuring camera of a positioning determining device is based in particular on the principal of a stereo camera, i.e. it comprises for instance two sensor elements (in particular CCD-chips) being distanced to each other, which receive light at different angles from an object (in particular from a marking element of the position determining device) such that the spatial position of the object can be reconstructed from the data of the sensor elements.

Thus, the spatial positions of the marking elements, i.e. the spatial coordinates thereof can be determined in a predefined coordinate system assigned to the position determining device. If the relative position of the marking elements in respect to the system, which they are attached to, is known, the position of the system can be deduced from the spatial positions of the marking elements. Such position determining devices are however known as such so that it is not discussed any further here.

In analogy, by using a position determining device, which serves for instance also for determining the spatial position of the second device (for instance the ultrasound head of a ultrasound device) the spatial position of the first device (for instance in form of an endoscopy device and in particular the endoscopy shaft thereof) can be determined, wherein ascertaining the second coordinates of the image points of the first image is effected by using the determined spatial position of the first device.

In a further exemplary embodiment of the invention generating the combined image comprises ascertaining coordinates of at least some of the image points of the first image in the second coordinate system, wherein the image points of the first image can be replaced or overlaid by image points of the second image with the corresponding second coordinates. Overlaying (cross fading) of the images can for instance be generated by adding the intensities of the image points of the first image and the second image. It is also conceivable that a user can define the degree of overlapping (degree of cross fading). The first image and/or the second image can be processed of course before their combination, for instance by using a filter or multiple filters (for instance for introducing a covering capacity factor).

The second image can be present also in form of a 3D image (for instance a 3D ultrasound image, for instance of a 3D reconstruction), which can be generated by detecting (by moving for instance the ultrasound head of an ultrasound device) of a multitude of image planes. According to the above described method (second) coordinates of the image plane of the first device are assigned to the spatial coordinates of the second image. In this variant of the invention a 3D view of the object is thus integrated into the second image. It is also possible that the device used for realizing a method according to the invention is designed such that a user can switch between the 3D fade-in or the fade-in of the current 2D image generated by the second device or can also completely switch off the integration of the second image.

It is also possible that when generating the combined image a sub-selection of image points of the first image is determined by a selection process and the determined image points are replaced or overlaid by image points of the second image with the corresponding second coordinates. For instance a sub-region is marked in the first image for selecting of image points to be replaced.

It is furthermore conceivable that (for instance in the first image) a sub-region (sub-section) of the object is selected (for instance marked) and the generation of the combined image is effected by replacing or overlaying image points of the first image within the sub-region of the object. In particular, the combination of the first and the second image (replacing and/or overlaying of the image points) is effected exclusively in the marked sub-region. A sub-section of the sub-region of the object illustrated by the first image is selected in particular as sub-region or a sub-region of the first image is ascertained, which corresponds to the selected sub-region (sub-section) of the object. It is conceivable that the sub-region of the object is selected as mentioned above by selecting a sub-region of the first image, for instance is marked in the first image.

The marking (segmentation) of the sub-region can for instance serve to mark a tissue structure (for instance a tumor) to be operated such that the information of the second image relevant for the surgeon is faded mainly or exclusively into said sub-region in order to provide on the one hand the desired depth information, yet on the other hand not to burden the surgeon with unnecessary image data. It is also conceivable that the marked sub-region follows a movement of the object. This is in particular enabled since marking elements can also be arranged at the object (for instance a patient to be operated) the position thereof can be followed by means of the mentioned position determining device such that the object position and thus when generating the combined image can be considered. Alternatively this can be achieved also without marking elements via a recognition of similar features in successive images and thus for instance via following a deformation of the object ("non-ridged image registration") see below.

It is conceivable that the sub-region of the object is selected by means of a reconstruction of the three-dimensional region of the object wherein the reconstruction is generated by using a multitude of images produced by the second device. For instance, the reconstruction of the three-dimensional region of the object comprises an interpolation between two time successive images of the second device depending on their respective spatial positions ascertained by means of the position determining device.

The interpolation of the two time successive images of the second device and/or a storage of data produced by the interpolation can be effected on a graphic card, wherein the interpolation is for instance calculated in parallel on the graphic card.

According to an exemplary embodiment of the invention marking of the object is effected by means of a light source (in particular a laser) of the first device, wherein the sub-region is marked by generating at least one light spot on the object by the light source. A multitude of light spots (support points) is in particular generated, wherein the light spots (light points) can be generated simultaneously or successively. If the light spots are generated successively, the first image showing the light spot is stored for instant for each light spot, wherein during the marking process (in particular in real time) or after finishing the marking process the corresponding first images are evaluated and the sub-region assembled from the successive produced light spots is determined in form for instance of a 2D polygon area or a volume.

According to an exemplary embodiment of the invention initial coordinates (in particular in the world coordinate system) of the sub-region are determined at the first time point and updated coordinates of the sub-region depending on the current position and/or shape of the object are determined at a second time point. In other words a following of the position and/or the shape of the object is effected, wherein the object is arranged for instance relative to the world coordinate system and thus to the coordinate system of the first device for instance by means of marking elements which are arranged relative to the object and are in relation thereto via rigid and non-rigid transformations.

It is also conceivable that the marking is effected by continuous leading a light beam generated by the light source over the object and a sequence of recordings recorded with the first device is evaluated.

A distance determining device of the first device can be used also for marking the spatial sub-region of the object being of interest. More specific the following steps are conducted:

marking a spatial sub-region of the object by means of a multitude of light spots;

ascertaining the spatial position of the first device by using a position determining device;

ascertaining the distance between the first device and the produced light spots by means of a position determining device of the first device;

ascertaining the spatial position of the sub-region by determining the spatial coordinates of the light spots in the coordinate system of the position determining device by using the ascertained spatial position of the first device and the ascertained distance.

The position determining device is in particular a clinical navigation system as already explained above. A distance determining device, with which in particular a distance between a section of the first device to be turned towards the object to be displayed and the object can be determined, comprises for instance means (in particular in form of a laser) for projecting the light structure onto the object to be projected and acts together for instance with a projecting optic and a camera of the first device.

The means for projecting are arranged in particular in respect to a projecting optic of the first device, which serves for projecting the object into the image plane of a camera of the first device, such that between the light bundle send out by the means for projecting and a light bundle reflected by the object, which falls from the object into a projecting optic of the first device, an angle (for instance 30°) or a distance between the optical axis of the light bundle and the optical access of the imaging optic exists such that the position of the image of the light pattern generated on the object in the image plane of the camera depends on the distance of the object to the first device. It is also in particular conceivable that by means of the distance determining device a position vector between a section of the first device and a section of the light structure projected by the distance determining device is determined, i.e. not only the distance is determined but also the orientation of a connecting line between said sections is determined.

A suitable first device (in form of an endoscopy device) which comprises such a position determining device is described in the already above mentioned German patent application, DE 10 2010 042 540.0 which is in so far also explicitly referenced.

It is however not mandatory that the sub-region of the object of interest is marked by using a light source. It is rather also conceivable that for instance the sub-region is drawn into the first image (present in digital form) first image (for instance by using a computer mouse or a drawing pencil) or that the sub-region is determined by means of a separate position determining device (for instance a navigated instrument).

It is possible that the sub-region is illustrated by using a ray-casting-method in the first and/or second image in order to provide a depth impression. The ray-casting-method is for instance a maximum intensity projection, an average intensity projection, a free definable transfer function and/or a surface projection.

It is also possible that the position determining device is connected to the first device (for instance is a part of the first device) or that the position determining device is a device separated from the first device (a separated instrument), i.e. is arranged in particular within a distance to the first device.

It is furthermore possible that the selection of the sub-region of interest is effected algorithmically, wherein the selection is ascertained for instance by applying a Boolean predicate function (for instance a threshold value function) onto image points of the second image and/or an image analytic method process (for instance a contour recognition process) onto the second image. The sub-region can thus be determined by defining a threshold value and selecting a plurality of image points of the second image (for instance in form of an ultrasound image) depending on the threshold value. For instance the predefined threshold value relates to the intensity of the image points, wherein for instance regions of the object are selected to which only image points of the second image are assigned, the intensity thereof exceeds (falls below) the threshold value. This automatic selection could be for instance used for selecting the tumor to be removed, wherein for selecting the tumor said tumor would have solely to be scanned for instance by ultrasound in order to obtain a corresponding 3D reconstruction of the tumor. Hereby a light source (in particular a laser) of the first device could serve to set a starting point for the 3D reconstruction.

The threshold value depending selection can be realized in particular in form of a filter which masks the background of the second image by means of the threshold value. This type of selection (segmentation) of a sub-region of the second image (i.e. the object to be displayed) can be in particular used to fade out a dark background of the second image, which would cover possible relevant image contents when combining with the first image. For instance the threshold value can also be adapted by a user.

It is also conceivable that the marked spatial sub-region of the object is extrapolated to a closed sub-region and a combined image is only produced if the region of the object recorded by the second device intersects the closed sub-region. For instance the marked sub-region is extrapolated to a closed cylinder. It is also possible that the closed sub-region is ascertained by means of the above described 3D reconstruction (for instance a tumor).

According to another exemplary embodiment of the invention information relating to the spatial position of the second device (for instance of the ultrasound head of an ultrasound device) is faded into the first image (for instance in form of an endoscopy image) in order for instance to provide assistance to a surgeon for aligning the second device ("augmented reality"—extended reality). For instance, the information faded in help the surgeon to capture a marked sub-region of the object of interest with the second device as completely as possible. Alternatively or additionally it is also possible that the second image (for instance an ultrasound image) is displayed on a separated display and information relating to the position of the first device is faded into said display. It is also conceivable that further information is faded in for instance relating to a laser beam of a position determining device of the first device, relating to a navigated instrument, i.e. an instrument the position thereof was determined in the world coordinate system, and/or preoperative image data.

Besides that the spatial position of at least one tool can be determined by means of the position determining device and the tool can be faded into the second image considering its spatial position and the spatial position of the second device. In particular the second image with the faded-in tool according to step e) is combined with the first image.

It is more over possible that a time delay of the image triggering of the first device, the second device and the position determination of the position determining device is ascertained and is available for the time coordination by a central processing unit for displaying the combined image.

The invention also relates also to a device for displaying an object, in particular for conducting a method described above, with:
a first device for generating a first image of at least one sub-region of the object;
a second device for generating at least one sub-region of a second image of the object;
a first coordinate ascertaining device for ascertaining first coordinates of at least some image points of the second image in a first coordinate system;
a second coordinate ascertaining device for ascertaining second coordinates of the image points of the second image by imaging the first coordinates into a second coordinate system, which is different from the first coordinate system and is assigned to the second device; and
an image-generating device for generating a combined image of the object from the first and the second image by using the ascertained second coordinates of the image points of the second image.

The first and the second coordinate ascertaining device are designed in particular in form of a software or a corresponding programmed electronic device (computer, microchip, and others). Similar, the image generating device can also be designed in the form of a software or a corresponding programmed hardware (for instance a graphics card).

The device comprises in particular also marking elements, which are arranged on the first device (for instance an endoscopy device) and/or the second device (for instance an ultrasound head of an ultrasonic device), wherein the one spatial position of the marking elements and thus the first device and/or the second device can be determined by means of position determining device. As already mentioned above, the position determining device is in particular a clinical navigation system, which comprises a position determining device as for instance a measuring camera.

BRIEF DESCRIPTION OF THE DRAWINGS

The invention is explained in more detail in the following by means of embodiments with reference to the figures.

DETAILED DESCRIPTION

Figure 1:
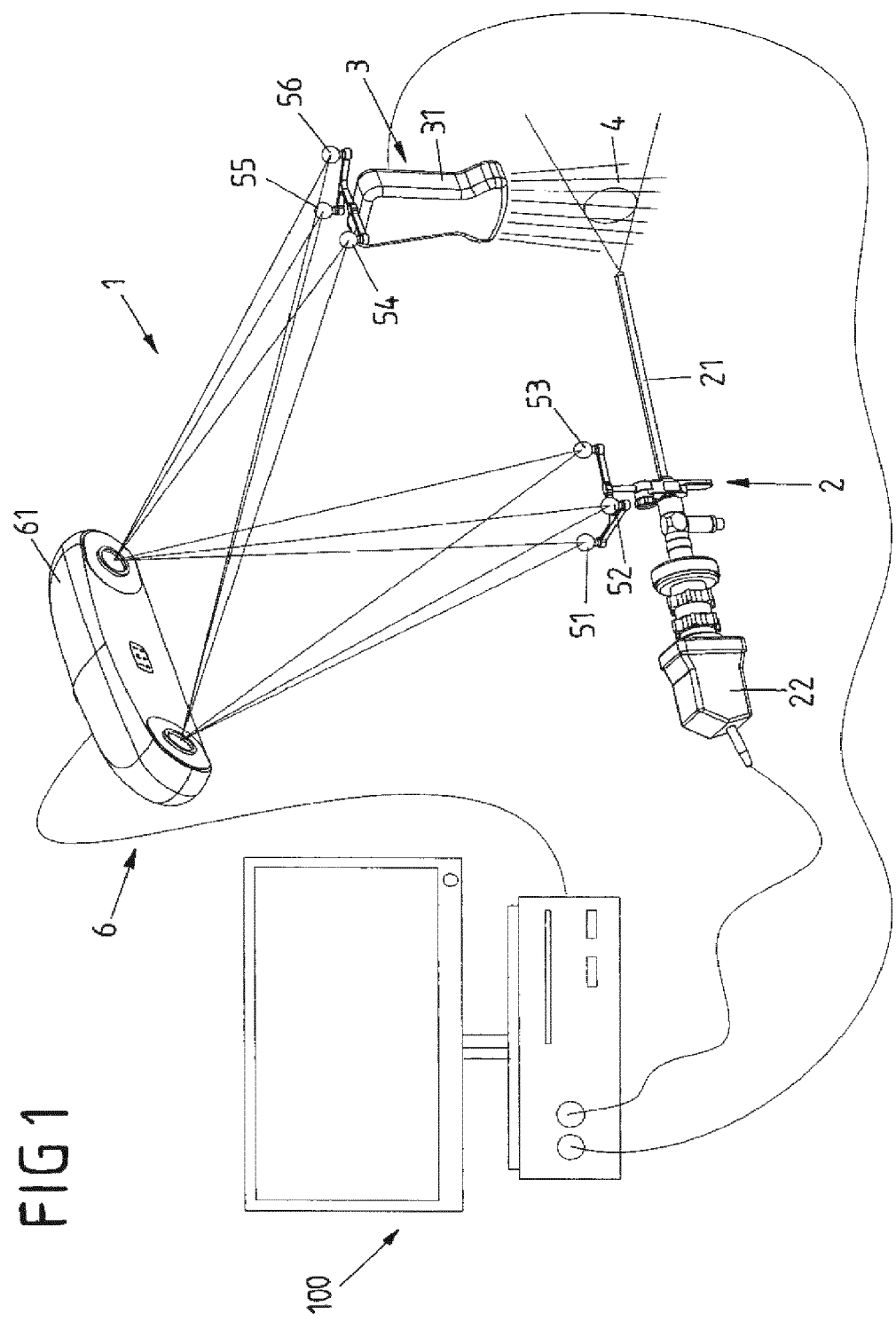
FIG. 1 shows a schematic view of a device according to an embodiment of the invention.

The device 1 according to the invention shown in FIG. 1 comprises a first device in form of an endoscopy device 2 (for instance in form of a hysteroscopy device) as well as a second device in form of an ultrasound device 3. The endoscopy device 2 as well as the ultrasound device 3 serve the generation of an image of an object in form of a tissue 4.

The endoscopy device 2 is a rigid endoscope, which has a rigid endoscopy shaft 21, in which an endoscopy optic for projecting an object into an image plane of a camera 22 of the endoscopy device 2 is located. The possible embodiment of the endoscopy device 2 is described in the already mentioned German patent application DE 10 2010 042 540.0. The camera 22 and the ultrasound device 3 are connected to a data processing system in form of a computer 100 for processing (for instance digitizing and filtering) and displaying the respective generated image data.

Marking elements in form of marking balls 51 to 53 are arranged on the endoscopy device 2. In analogy marking balls 54 to 56 are arranged also at an ultrasound head 31 of the ultrasound device 3, wherein the marking balls 51 to 56 allow a determination of the position, that means the side where the respective device is located as well as the alignment of the respective device. For this purpose the device 1 according to the invention comprises a position determining device in form of a clinical navigation system 6 which comprises a measuring camera in form of a stereo camera 61. The position of the marking balls 51 to 53 attached to the endoscopy device 2 and the marking balls 54 to 56 arranged at the ultrasound head 31 of the ultrasound device 3 and thus of the endoscopy device 2 and the ultrasound device 3 can be determined by means of the stereo camera 61.

In particular, the position of the image plane of the endoscopy camera 22 as well as the position of the region (for instance a plane) of the tissue 4 captured by the ultrasound head 31 is also known by determining the position of the endoscopy device 2 and is updated for instance in real time by (manual) movement of the endoscopy device 2 and/or the ultrasound head 31. After calibrating the endoscopy device 2 and the ultrasound device 3 it is thus possible to combine the ultrasound image generated by the ultrasound device 3 perspective correct with the endoscopy image generated by the endoscopy device 2. For this purpose spatial coordinates in a spatial coordinate system assigned to the position determining device 6 (of the measuring chamber 61) are assigned to (first) coordinates of image points of the ultrasound image, wherein the spatial coordinates to be assigned to the ultrasound image points are coordinates of points of the region of the tissue 4 captured by the ultrasound device 3.

These spatial coordinates assigned to the image points of the ultrasound image are projected by using a (simulated) projection, which was ascertained by the calibration of the endoscopy device 2, into the (virtual) image plane of the camera 22, i.e. into a plane, which corresponds to the image plane of the camera 22 in respect to its position, and (second) coordinates of the ultrasound image points are determined in respect to the image plane of the camera 22. By replacing and/or overlaying image points of the endoscopy image generated by the endoscopy device 2 by image points of the ultrasound image, which comprise corresponding (second) coordinates (i.e. coordinates in respect to the image plane of the camera 22) a combined image of the tissue 4 is generated.

Figure 2:
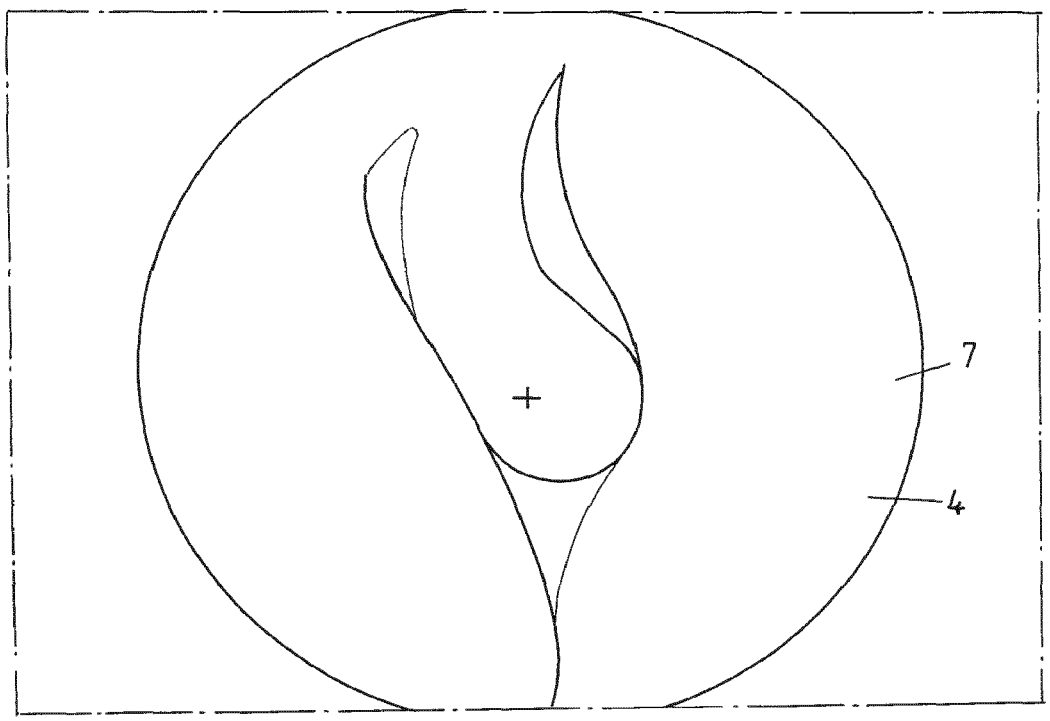
FIG. 2 shows an endoscopy image of a tissue generated by the device of FIG. 1.
Figure 3:
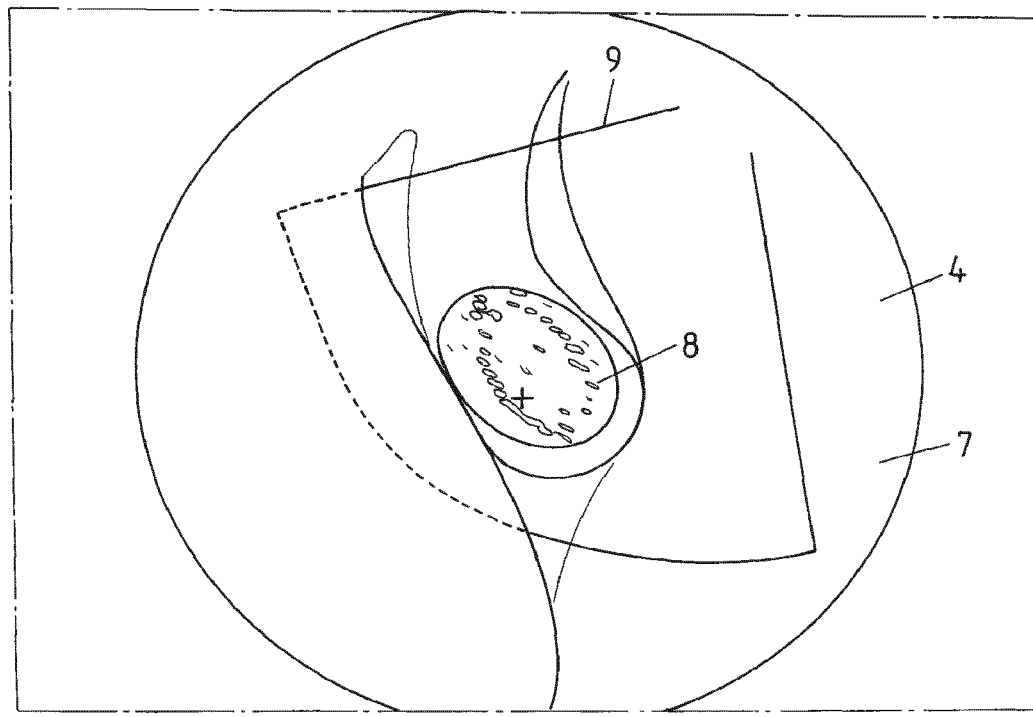
FIG. 3 shows a combined image of the tissue generated by an endoscopy and ultrasound image.

An example of such perspective correct combined image is shown in FIG. 3, wherein FIG. 3 is based on an endoscopy image recorded by the endoscopy device 2, which is shown in FIG. 2.

According to FIG. 3 a sub-region of the endoscopy image 7 is replaced by an ultrasound image 8, wherein the coordinates of the points of the original ultrasound image were transformed according to the above described method. The position correct integration of the ultrasound image into the endoscopy image enabled in this manner provides in addition to the optical information of the endoscopy image a depth information of the tissue. The depth of the ultrasound image, i.e. position of the plane, which is captured by the ultrasound head and is displayed in the ultrasound image 8, can be changed by a manual movement of the ultrasound head 31 of the ultrasound device 3. It is also conceivable that instead of the shown 2D ultrasound image a 3D reconstruction of the tissue is integrated.

As explained above it is possible that a sub-region of the tissue 4 is selected and the endoscopy image 7 is replaced or overlaid only in a section of the ultrasound image 8, which corresponds to the selected sub-region of the tissue 4. The selection of the sub-region of interest can be effected for instance by means of a distance determining device of the endoscopy device, wherein light spots can be generated on the tissue 4 by a laser of the distance determining device, wherein said light spots mark the sub-region. In FIGS. 2 and 3 the position of the light spot is characterized by a cross. For instance, the marking is done by means of the laser such that multiple sides of the tissue are scanned by the laser and are registered, as already explained above.

Additional information can also be faded into the combined image, for instance an information relating to the alignment of the ultrasound head 31. As shown in FIG. 3 this can be done for instance by fading in a structure 9, which characterize the position of the cutting cone 9 captured by the ultrasound head 31. The structure 9 is an "Augmented reality" fade-in. Further fade-ins are conceivable which for instance indicate a direction along which the ultrasound head has to be moved in order to capture a marked sub-region of the tissue.

Figure 4:
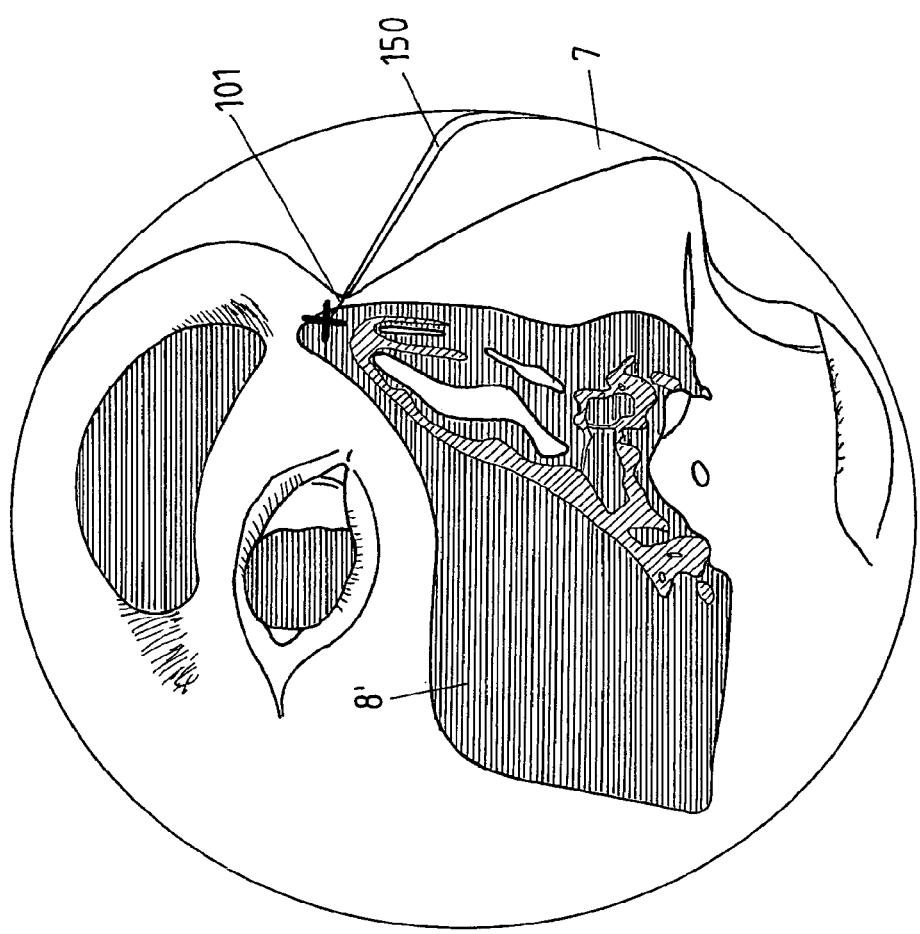
FIGS. 4 and 5 show further examples of a combined image generated by the method according to the invention.
Figure 5:
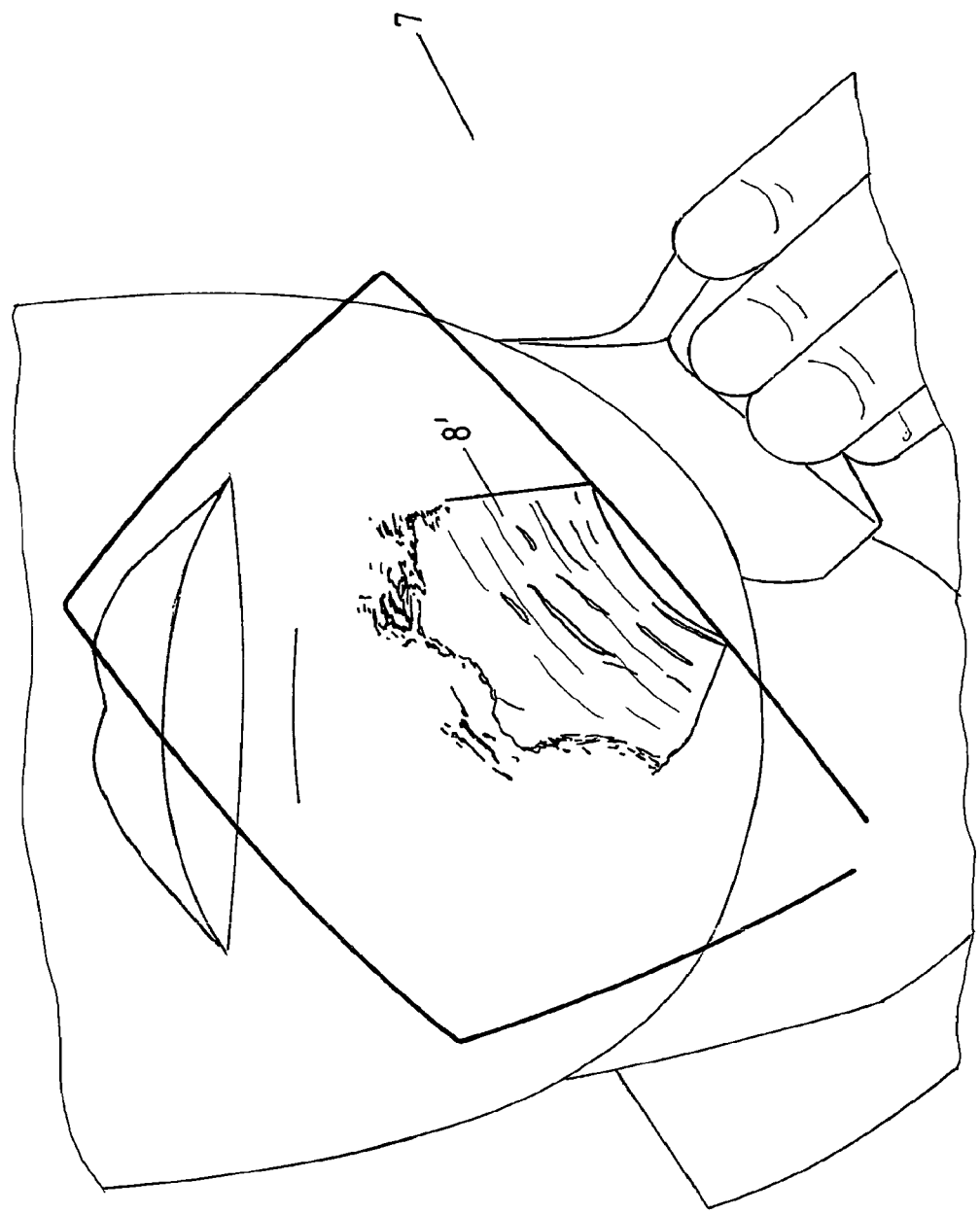

FIGS. 4 and 5 show in each case a combined image with a preoperative CT image 8' (recorded for instance by an endoscope or another camera) which is faded into a first image 7.

Furthermore, a navigated instrument 150 is displayed in FIG. 4, i.e. an instrument, the spatial position thereof was determined by a navigation system (see above), wherein the instrument 150 comprises in particular corresponding navigation marking elements. The position of the instrument (tool) 150 is characterized in the combined image in a correct position in respect to the CT image 8' by a line type marking 101. Besides that an elongation of the axis of the instrument 150 is marked in respect to the CT image 8' (cross).

LIST OF REFERENCE SIGNS

1 Device
2 Endoscopy device
3 Ultrasound head
4 Tissue
6 clinical navigation system
7 Endoscopy image
8 Ultrasound image
8' preoperative CT image
9 Structure
21 Endoscopy shaft
22 Camera
31 Ultrasound head
61 Stereo camera
51-56 Marking balls
100 Computer
101 Marking
150 Instrument

What is claimed is:
1. A method for determining image points while displaying an object, in particular biological tissue, comprising the steps of:
   a) generating a first image of at least one sub-region of the object with a first imaging device;

b) generating a second image of at least one sub-region of the object with a second imaging device;

c) ascertaining first coordinates of at least some of the image points of the second image in a first coordinate system;

d) ascertaining second coordinates of at least some of the image points of the second image by projecting the first ascertained coordinates in a second coordinate system which is different from the first coordinate system and which is assigned to the first imaging device; and e) generating a combined image of the object from the first and the second images using the ascertained second coordinates of the image points of the second image, wherein selection of the image points to be combined is achieved by selecting a sub-region of the object which is marked successively in a marking process including:

using the first imaging device that comprises a navigated light source to generate a multitude of distinct light spots on the object as supporting points, or using a separate navigated instrument to mark the object with a plurality of supporting points, so that generation of the combined image is achieved following the marking process by replacing or overlaying image points of the first image within the selected sub-region with image points of the second image.

2. The method of claim 1, wherein the first imaging device is an intraoperative imaging device and the first image is an intraoperative image.

3. The method of claim 1, wherein the first imaging device is selected from the group consisting of: a computed tomography (CT) device, a magnetic resonance tomography (MRT) device, a nuclear radiological device, and a single photon emission computed tomography (SPECT) device.

4. The method of claim 1, wherein the second imaging device is an endoscopy device and the second image is an endoscopy image.

5. The method of claim 1, wherein the second imaging device is an ultrasound device and the second image is an ultrasound image.

6. The method of claim 1, wherein the second imaging device is an intraoperative imaging device and the second image is an intraoperative image.

7. The method of claim 1, wherein the second imaging device is selected from the group consisting of: a computed tomography (CT) device, a magnetic resonance tomography (MRT) device, a nuclear radiological device, and a single photon emission computed tomography (SPECT) device.

8. The method of claim 1, wherein the first imaging device is an ultrasound device and the first image is an ultrasound image.

9. The method of claim 8, wherein the second imaging device is an intraoperative imaging device and the second image is an intraoperative image.

10. The method of claim 9, wherein the second imaging device is selected from the group consisting of: a computed tomography (CT) device, a magnetic resonance tomography (MRT) device, a nuclear radiological device, and a single photon emission computed tomography (SPECT) device.

11. The method of claim 1, further comprising a position determining device that comprises a measurement device and a marking element coupled to the first imaging device and/or second imaging device; and said method further comprises determining a spatial position of the first imaging device and/or the second imaging device using the measurement device to track the marking elements of the position determining device.

12. The method of claim 1, further comprising a position determining device that is connected to the first imaging device and/or the second imaging device; and said method further comprises determining a spatial position of the first imaging device and/or the second imaging device using the position determining device.

13. The method of claim 1, wherein determining image points is achieved by using a sub-region of the object which is marked successively in a marking process:

with a multitude of light spots as supporting points, wherein the first imaging device comprises a navigated light source, so that generation of the combined image is achieved following the marking process by replacing or overlaying image points of the first image within the selected sub-region with image points of the second image.

14. The method of claim 1, wherein determining image points is achieved by using a sub-region of the object which is marked successively in a marking process:

by marking a sub-region of the object with a plurality of supporting points with a separate navigated instrument, so that generation of the combined image is achieved following the marking process by replacing or overlaying image points of the first image within the selected sub-region with image points of the second image.

15. The method of claim 1, wherein ascertaining of the second coordinates comprises determining a spatial position of the second imaging device with a position determining device and projecting the first coordinates of the image points in spatial coordinates in a spatial coordinate system assigned to the position determining device.

16. The method of claim 15, wherein the sub-region is selected via a reconstruction of a three-dimensional area of the object, wherein the reconstruction is generated by using a plurality of images generated by the second imaging device.

17. The method of claim 16, wherein the reconstruction of the three-dimensional region of the object comprises an interpolation between two time successive images of the second imaging device depending on their respective spatial positions ascertained via the position determining device.

18. The method of claim 15, wherein a common spatial reference coordinate system of the first imaging device and the second imaging device is not defined by the position determining device, but by at least one marking element attached relative to the object which can be captured by the position determining device such that a movement of the object can be compensated.

19. A method for determining image points while displaying biological tissue, said method comprising the steps of:

a) generating a first image of at least one sub-region of the biological tissue with an intraoperative device;

b) generating a second image of at least one sub-region of the biological tissue with an ultrasound device;

c) ascertaining first coordinates of at least some of the image points of the second image in a first coordinate system;

d) ascertaining second coordinates of at least some of the image points of the second image by projecting the first ascertained coordinates in a second coordinate system which is different from the first coordinate system and which is assigned to the intraoperative device; and e) generating a combined image of the biological tissue from the first and the second image using the ascertained second coordinates of the image points of the second image, wherein determining image points is achieved by using a sub-region of the biological tissue of interest which is marked successively using a marking process including:

marking the biological tissue with a multitude of discrete light spots as supporting points with the intraoperative device that comprises a navigated light source, or marking a sub-region of the biological tissue of interest with a plurality of supporting points with a separate position determining device, so that generation of the combined image is achieved following the marking process by replacing or overlaying image points of the first image within the selected sub-region with image points of the second image.

20. The method of claim 19, wherein the intraoperative device is selected from the group consisting of: a computed tomography (CT) device, a magnetic resonance tomography (MRT) device, a nuclear radiological device, and a single photon emission computed tomography (SPECT) device.

21. A method for determining image points while displaying an object, in particular biological tissue, comprising the steps of:

a) generating a first image of at least one sub-region of the object with a first imaging device;
b) generating a second image of at least one sub-region of the object with a second imaging device;
c) ascertaining first coordinates of at least some of the image points of the second image in a first coordinate system;
d) ascertaining second coordinates of at least some of the image points of the second image by projecting the first ascertained coordinates in a second coordinate system which is different from the first coordinate system and which is assigned to the first imaging device; and
e) generating a combined image of the object from the first and the second images using the ascertained second coordinates of the image points of the second image, wherein selection of the image points to be combined is achieved by selecting a sub-region of the object which is marked successively in a marking process including:

using the first imaging device that comprises a laser to generate a multitude of distinct light spots on the object as supporting points, or using a separate navigated instrument to mark the object with a plurality of supporting points, so that generation of the combined image is achieved following the marking process by replacing or overlaying image points of the first image within the selected sub-region with image points of the second image.

* * * * *